US012557979B2

(12) United States Patent
Ng et al.

(10) Patent No.: US 12,557,979 B2
(45) Date of Patent: Feb. 24, 2026

(54) VIDEO LARYNGOSCOPE WITH WINDOW FOR INFRARED PAIRING

(71) Applicant: Covidien LP, Mansfield, MA (US)

(72) Inventors: Michael Ng, Hong Kong (HK); Peter Douglas Colin Inglis, Bouder, CO (US); Jürgen Van Vlem, Hong Kong (HK)

(73) Assignee: Covidien LP, Mansfield, MA (US)

( * ) Notice: Subject to any disclaimer, the term of this patent is extended or adjusted under 35 U.S.C. 154(b) by 396 days.

(21) Appl. No.: 18/160,048

(22) Filed: Jan. 26, 2023

(65) Prior Publication Data

US 2023/0248235 A1 Aug. 10, 2023

Related U.S. Application Data

(60) Provisional application No. 63/267,642, filed on Feb. 7, 2022.

(51) Int. Cl.
A61B 1/267 (2006.01)
A61B 1/00 (2006.01)
A61B 1/05 (2006.01)

(52) U.S. Cl.
CPC .......... A61B 1/267 (2013.01); A61B 1/00011 (2013.01); A61B 1/00048 (2013.01); A61B 1/00052 (2013.01); A61B 1/05 (2013.01)

(58) Field of Classification Search
CPC ..................................................... A61B 1/267
See application file for complete search history.

(56) References Cited

U.S. PATENT DOCUMENTS

| | | | |
|---|---|---|---|
| 8,194,122 B2 | 6/2012 | Amling et al. |
| 8,652,033 B2 | 2/2014 | Berci et al. |
| 8,715,172 B1 | 5/2014 | Girgis |
| 8,746,239 B2 | 6/2014 | Yoshida |
| 8,827,899 B2 | 9/2014 | Farr et al. |
| 8,982,199 B2 | 3/2015 | Amling et al. |

(Continued)

FOREIGN PATENT DOCUMENTS

| | | |
|---|---|---|
| EP | 2433553 A1 | 3/2012 |
| JP | 2014210085 A | 11/2014 |
| WO | 2020/005890 A1 | 1/2020 |

OTHER PUBLICATIONS

Ambu_aScope_3_Large_Brochure_4963605 (Oct. 2017).

(Continued)

*Primary Examiner* — Tessa M Matthews

(57) ABSTRACT

A video laryngoscope including a display portion, a handle, and a camera assembly. The display portion includes a housing having a patient-facing side and a user-facing side. A display screen is disposed on the user-facing side and configured to display images captured by the camera assembly. An infrared window is disposed at another position on the video laryngoscope, such as on the patient-facing side of the housing. Infrared signals for pairing the video laryngoscope to other devices, such as monitors or external display screens, may be transmitted through the infrared window. For instance, an infrared receiver of the video laryngoscope may receive infrared signals through the infrared window and/or an infrared transmitter of the video laryngoscope may transmit infrared signals through the infrared window.

19 Claims, 7 Drawing Sheets

(56) References Cited

U.S. PATENT DOCUMENTS

| | | | |
|---|---|---|---|
| 9,123,155 B2 | 9/2015 | Cunningham et al. | |
| 9,498,112 B1 | 11/2016 | Stewart et al. | |
| 9,538,908 B2 | 1/2017 | Allyn et al. | |
| 9,687,141 B2 | 6/2017 | McGrath | |
| 9,820,641 B2 | 11/2017 | McGrath | |
| 10,010,379 B1 | 7/2018 | Gibby et al. | |
| 10,149,957 B2 | 12/2018 | Runnels | |
| 10,307,599 B2 | 6/2019 | Schilling | |
| 2007/0197896 A1 | 8/2007 | Moll et al. | |
| 2007/0236514 A1 | 10/2007 | Agusanto et al. | |
| 2008/0101153 A1* | 5/2008 | Swisher | B28C 7/064 |
| | | | 366/47 |
| 2008/0177146 A1 | 7/2008 | Chen | |
| 2008/0177148 A1 | 7/2008 | Chen et al. | |
| 2008/0312507 A1 | 12/2008 | Kim | |
| 2011/0130632 A1 | 6/2011 | McGrail et al. | |
| 2011/0137127 A1 | 6/2011 | Schwartz | |
| 2011/0245609 A1 | 10/2011 | Laser | |
| 2011/0275894 A1* | 11/2011 | Mackin | A61B 1/00016 |
| | | | 600/109 |
| 2013/0057667 A1 | 3/2013 | McGrath | |
| 2013/0267838 A1 | 10/2013 | Fronk et al. | |
| 2014/0031700 A1 | 1/2014 | Ferrantelli | |
| 2014/0160261 A1 | 6/2014 | Miller et al. | |
| 2014/0275760 A1 | 9/2014 | Lee et al. | |
| 2014/0378763 A1 | 12/2014 | Atarot | |
| 2016/0199009 A1 | 7/2016 | Gilboa | |
| 2016/0279365 A1 | 9/2016 | Esnouf | |
| 2017/0055809 A1 | 3/2017 | Omoto | |
| 2017/0209071 A1 | 7/2017 | Zhao et al. | |
| 2017/0258313 A1 | 9/2017 | McGrath | |
| 2018/0193102 A1 | 7/2018 | Inoue | |
| 2018/0292199 A1 | 10/2018 | Tojo et al. | |
| 2018/0296281 A1 | 10/2018 | Yeung et al. | |
| 2018/0324352 A1 | 11/2018 | Furuhata | |
| 2019/0133430 A1 | 5/2019 | Inglis et al. | |
| 2019/0142262 A1* | 5/2019 | Inglis | A61B 1/00048 |
| | | | 600/188 |
| 2020/0015925 A1* | 1/2020 | Scheib | A61B 1/07 |
| 2020/0029793 A1 | 1/2020 | McGrath | |
| 2020/0178786 A1* | 6/2020 | Sabetrasekh | A61B 1/00073 |
| 2020/0195903 A1 | 6/2020 | Komp et al. | |
| 2020/0275824 A1 | 9/2020 | Tata | |
| 2020/0367742 A1 | 11/2020 | McGrath | |
| 2020/0383561 A1 | 12/2020 | McGrath | |
| 2021/0052140 A1 | 2/2021 | Tata | |
| 2021/0121155 A1 | 4/2021 | Maguire | |
| 2021/0127949 A1 | 5/2021 | Tata | |
| 2021/0128033 A1 | 5/2021 | Tata | |
| 2021/0137350 A1 | 5/2021 | Inglis | |
| 2021/0257856 A1 | 8/2021 | Ng | |
| 2021/0259536 A1 | 8/2021 | Inglis | |
| 2021/0275008 A1 | 9/2021 | McGrath | |
| 2021/0318382 A1 | 10/2021 | McGrath | |
| 2022/0110504 A1 | 4/2022 | Inglis | |
| 2022/0225859 A1 | 7/2022 | Phillips | |
| 2022/0257092 A1 | 8/2022 | Ng | |
| 2022/0354380 A1 | 11/2022 | Tata | |
| 2023/0029630 A1 | 2/2023 | Ng | |

OTHER PUBLICATIONS

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS One | https://doi.org/10.1371/journal.pone.0186691 (Nov. 3, 2017).

International Search Report for International Application No. PCT/IB2023/051046 mailed Jul. 3, 2023 (15 pages).

* cited by examiner

VIDEO LARYNGOSCOPE WITH WINDOW FOR INFRARED PAIRING

CROSS-REFERENCE TO RELATED APPLICATIONS

This application claims the benefit of U.S. Provisional Application No. 63/267,642 filed Feb. 7, 2022, entitled "Video Laryngoscope with Window for Infrared Pairing," which is incorporated herein by reference in its entirety.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of any kind.

A laryngoscope is a device used by a medical professional to view a patient's oral cavity to facilitate intubation. During intubation, a tracheal tube (e.g., endotracheal tube, tracheostomy tube, or transtracheal tube) is inserted through the patient's oral or nasal cavity and into the patient's trachea. Video laryngoscopes include a camera on a portion of the laryngoscope to obtain an image of the oral cavity. The image may then be displayed during the intubation procedure to enable the medical professional to visualize the oral cavity and to facilitate manipulation and insertion of the tracheal tube. A video laryngoscope may include an integral display that is in the line-of-sight of the medical professional so that the patient airway is viewable on the display screen in real-time to facilitate navigation and insertion of tracheal tube within the airway.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an example, the technology relates to a video laryngoscope that includes a handle; a housing coupled to the handle; a display screen coupled to the housing; a camera coupled to the handle; an infrared window provided in the handle or the housing; an infrared receiver, disposed in the video laryngoscope, that receives an infrared signal through the infrared window; and a processor, disposed in the video laryngoscope, that validates a pairing between the video laryngoscope and an external device based on the infrared signal.

In an example, the housing comprises a user-facing side and a patient-facing side, the display screen is positioned in the user-facing side; and the infrared window is positioned in the patient-facing side. In another example, the housing includes a user-facing side, a patient-facing side, a top side, and a bottom side, the display screen is positioned in the user-facing side; and the infrared window is positioned in at least one of the patient-facing side or the top side. In a further example, the infrared window is positioned in the top side. In still another example, the infrared window is entirely encompassed within a quadrant of the patient-facing side. In yet another example, the quadrant is a lower-right quadrant of the patient-facing side. In a still further example, the infrared window is provided in the handle. In still yet another example, the display screen is configured to display images captured by the camera.

In another aspect, the technology relates to a video laryngoscope that includes a handle; a camera coupled to the handle; and a display portion comprising a housing coupled to the handle, the housing having a user-facing side and a patient-facing side. The housing includes a display screen positioned on the user-facing side; and an infrared window positioned on the patient-facing side. The video laryngoscope further includes at least one an infrared receiver or an infrared transmitter disposed within the housing and optically aligned with the infrared window; and a processor, disposed within video laryngoscope, that validates a pairing between the video laryngoscope and an external device based on an infrared signal.

In an example, the patient-facing side is substantially planar. In yet another example, the housing has a height and a width; the infrared window has a height and a width; and the height of the housing is less than 7 times greater than the height of the infrared window. In still another example, the width of the housing is less than 6 time greater than the width of the infrared window. In a further example, the infrared window is entirely encompassed within a quadrant of the patient-facing side. In still yet another example, the video laryngoscope further includes an adhesive tape, and the housing defines a recessed portion and a ledge; and the adhesive tape is positioned between the infrared window and the ledge. In a still further example, the infrared window is translucent to an infrared spectrum and opaque to a human-visible spectrum.

In another aspect, the technology relates to a video laryngoscope system. The system includes a video laryngoscope that includes a housing; an infrared window in the housing; and an infrared receiver, disposed within the housing, optically aligned with the infrared window. The system further includes an external display screen comprising an infrared emitter configured to be activated to emit an infrared signal comprising identification information of the external display screen. The video laryngoscope is configured to receive the infrared signal through the infrared window provided in a housing of the video laryngoscope.

In an example, the infrared window is disposed over an opening in the housing. In a further example, the video laryngoscope further comprises a display screen coupled to the housing. In another example, the display screen is positioned on a front side of the housing and the infrared window is disposed on a back side of the housing. In still another example, the video laryngoscope further includes a handle pivotably coupled to the housing; and a camera assembly coupled to the handle.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
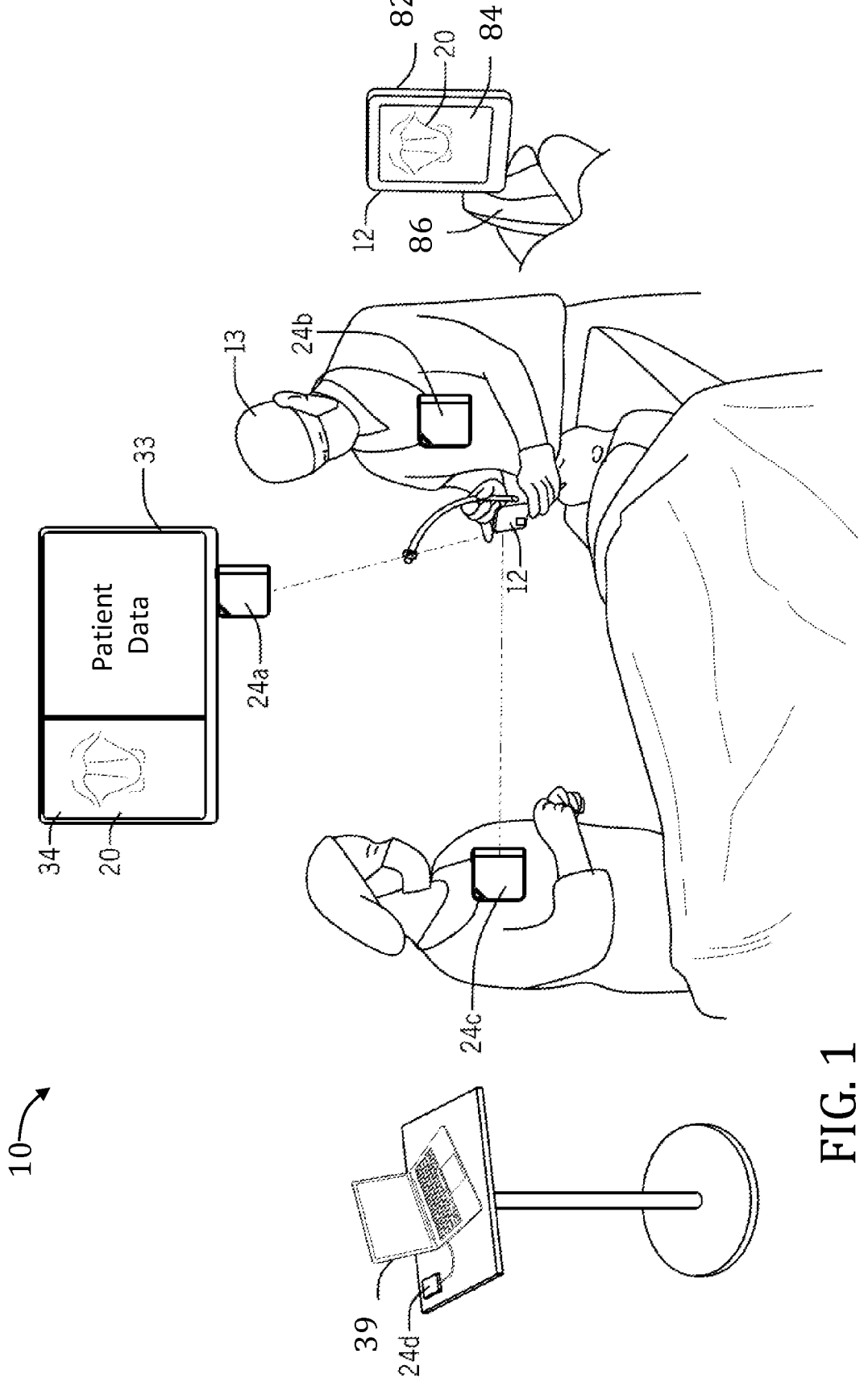
FIG. 1 is a schematic illustration of an example patient environment including a video laryngoscope with infrared communication capabilities.

The present disclosure relates generally to medical devices with wireless communication, such as video laryngoscopes with components for infrared pairing. During an intubation procedure, images acquired by a video laryngoscope can provide important context to other medical professionals. Accordingly, in certain clinical settings, such as in an operating room or when intubating a patient, it may be beneficial to display medical device data obtained by a wireless medical device (such as a video laryngoscope) on a separate screen, thereby allowing multiple medical professionals to view the data in real time. In some cases, the video laryngoscope can be paired with a relatively larger external display that duplicates the display screen of the video laryngoscope such that other medical professionals can track the progress of the intubation or other airway procedure in real time on the external display.

In this manner, the airway status of the patient is visible to other clinicians, who may view these images as part of training, to offer relevant information or advice to the laryngoscope operator, and/or to prepare for subsequent procedures based on the progress of the intubation. In one example, a surgical team in a staging area may move into position and prepare initial steps of a surgical procedure based on video laryngoscope images that are indicative of near-completion of an intubation. In another example, the laryngoscope operator can be advised of potential intubation difficulties based on the visible airway anatomy.

Provided herein are systems and methods that incorporate an infrared receiver and/or infrared transmitter to facilitate pairing between medical devices during a clinical procedure, such as to share video data from a video laryngoscope to an external display screen. The medical device may pair with an external display screen via exchanging or receiving identification information which is used to identify or validate the devices and/or to establish wireless communication permissions or protocols between these devices. The present techniques provide systems and methods of communication and pairing between devices, e.g., video laryngoscopes, display screens, databases, computers, relays, transceivers, and other devices.

By using the infrared pairing techniques described herein, the pairing and communication process may be made more efficient and secure. For instance, by utilizing an infrared pairing technique, the devices that may be paired together generally must be located in the same room or location. As an example, devices in one operating room are prevented from being paired to devices in another operating room because the infrared signals cannot pass through the walls between the operating rooms. Thus, the present technology substantially helps prevent unintentional pairing a video laryngoscope in one operating room with an external display screen of another operating room, which would cause confusion and potentially (albeit unintentionally) share confidential medical information with persons in the other operating room.

In addition, the exchange of pairing information via infrared means reduces the number of user interactions that are required to complete the pairing of devices. For example, other types of wireless pairing, such as the BLUETOOTH protocol, often require significant user input of codes of other information. Such user input processes can be cumbersome to a surgeon and potentially delay surgeries or increase occupation times of operating rooms. With the infrared pairing, those types of codes and user interactions may be eliminated or significantly reduced.

FIG. 1 is a schematic illustration of a patient environment that includes a video imaging system 10 that wirelessly pairs with other devices such as display screens. The patient environment may be any room where an intubation is being performed, such as a medical suite in a hospital or other care setting, an operating or other procedure room, patient recovery room, an emergency intubation setting, or other environments. The video imaging system 10 may include a video laryngoscope 12 that, in operation, is used for airway visualization of a patient. The video imaging system 10 may additionally or alternatively be used with other patient visualization instruments that acquire patient images, such as endoscopes or other imaging tools.

A laryngoscope operator 13 holds a body or handle 86 of the laryngoscope 12 coupled to a display portion 82 having a display screen 84 that faces the operator. The opposite side of the display portion 82 (e.g., a patient-facing side) may include an infrared window through which infrared signals for pairing may be transmitted. Acquired airway images 20 are displayed on the display screen 84. The video laryngoscope 12 may be used as part of an intubation procedure to advance a tracheal tube into a patient airway to secure the airway for mechanical ventilation. Accordingly, the operator 13 of the video laryngoscope 12 performs the intubation and directly manipulates the endotracheal tube within the patient's airway, and other clinicians in the patient environment assist the laryngoscope operator, monitor a condition of the patient, prepare or adjust medical equipment in the patient environment, and/or wait until the airway is secured to perform other procedures or interventions.

The airway images 20 acquired by the video laryngoscope 12 are visible on the laryngoscope display screen 84 that is positioned in the operator's line of sight. In addition, the acquired airway images 20 may be communicated to a monitor, external display, and/or external computer 39. The external display 33 and/or the external computer 39 may include devices such as a patient vital sign monitor, a laptop, a tablet, a display screen, or other computing device separate from the video laryngoscope 12. The external display 33 may also receive other data, such as images from one or more environmental cameras or other patient data. In an example, the external display 33 receives the airway images 20 and the additional data and generates a combined view 34.

The airway images 20 may be communicated during operation of the video laryngoscope 12, such as in response to actuating a power button that enables a medical professional to power the video laryngoscope 12 off and on and/or after interaction an input device (such as a touch or proximity sensor, e.g., capacitive sensor, proximity sensor, or the like) that enables the medical professional operating the video laryngoscope 12 to provide inputs or commands.

The environment or system 10 may also include one or more wireless hubs 24, such as wireless hub 24a, wireless hub 24*b,* wireless hub 24*c,* and wireless hub 24*d.* The wireless hub 24, as provided herein, may be implemented as a puck, wand, dongle, module, or disc having a housing that can be sized and shaped to be portable and, in examples, handheld or lightweight. The wireless hub 24 can be housed separately from coupled or paired devices. The wireless hub 24 may be multifunctional or capable of operating in one of a plurality of operating modes. Notably, each illustrated wireless hub 24 can be a same type of device that is operating differently based on a pairing arrangement of the wireless hub 24 with other devices. In one arrangement, a wireless hub 24*a* in a streaming operating mode is coupled to an external display 33 and is also wirelessly paired to the video laryngoscope 12. The acquired images 20 from the video laryngoscope 12 are streamed from the video laryngoscope 12 to the wireless hub 24*a* and provided from the wireless hub 24*a* to the external display 33 for display on all or a portion of an external display screen 33. Thus, in an example, the images 20 displayed on the laryngoscope display screen 84 and streamed to the external display 33 are substantially the same real-time images. In the illustrated example, the wireless hub 24*a* is directly coupled to an input port of the external display 33. However, other coupling arrangements (e.g., wireless, wired) are also contemplated.

The system 10 may additionally or alternatively include wireless hubs 24*b,* 24*c* in a data transfer operating mode that are wirelessly paired to the video laryngoscope 12, are not coupled to the external display 33, and that are operating as personal data storage devices to receive images 20. Thus, the wireless hubs 24*b,* 24*c* are paired only to the video laryngoscope 12, and not to any other devices, in the data transfer operating mode. In the illustrated example, the wireless hubs 24*b,* 24*c* are worn on lanyards by different medical professionals participating in the medical procedure and who wish to receive the images 20.

Figure 2:
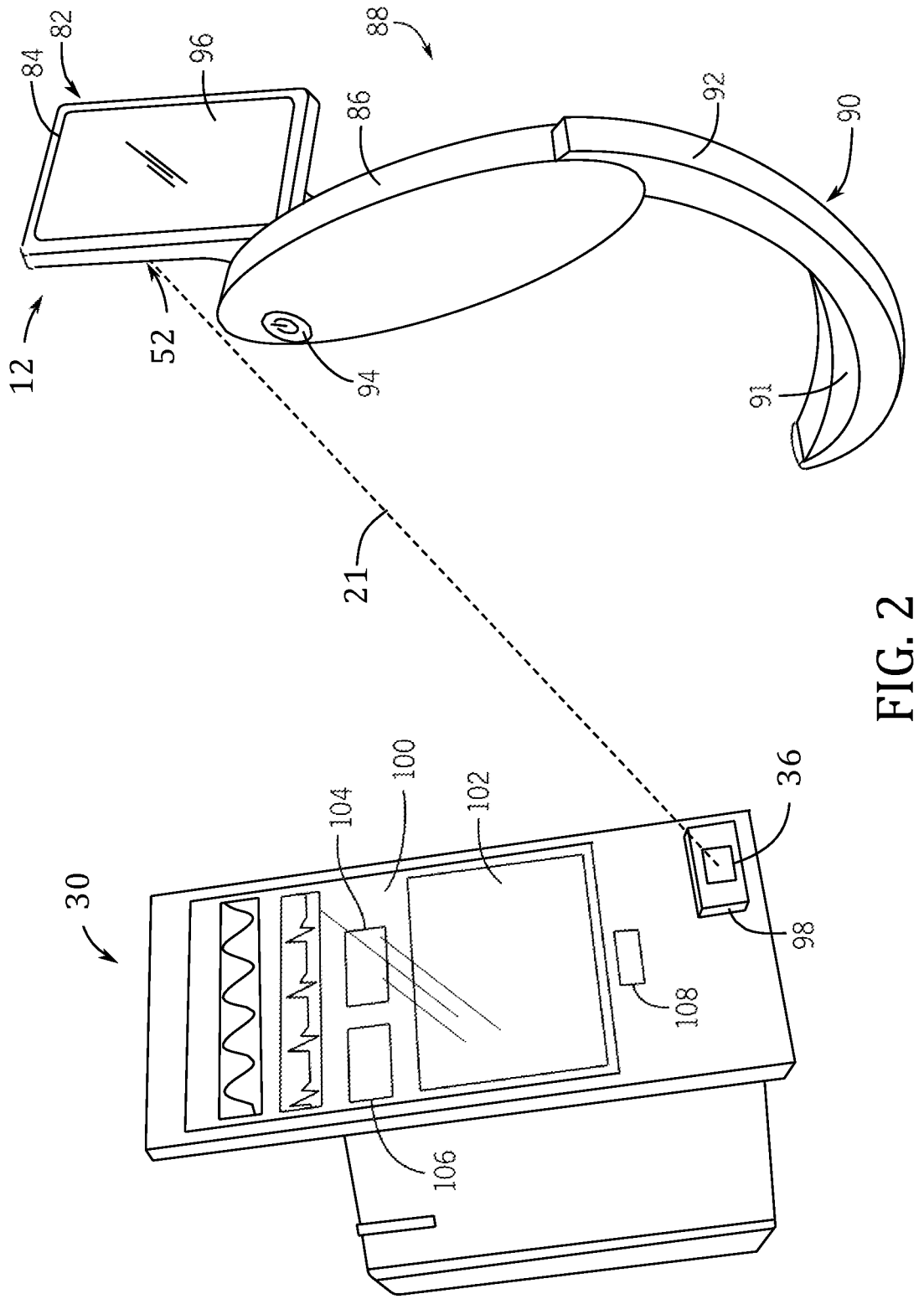
FIG. 2 depicts an example video laryngoscope in communication with an example monitor.
Figure 3:
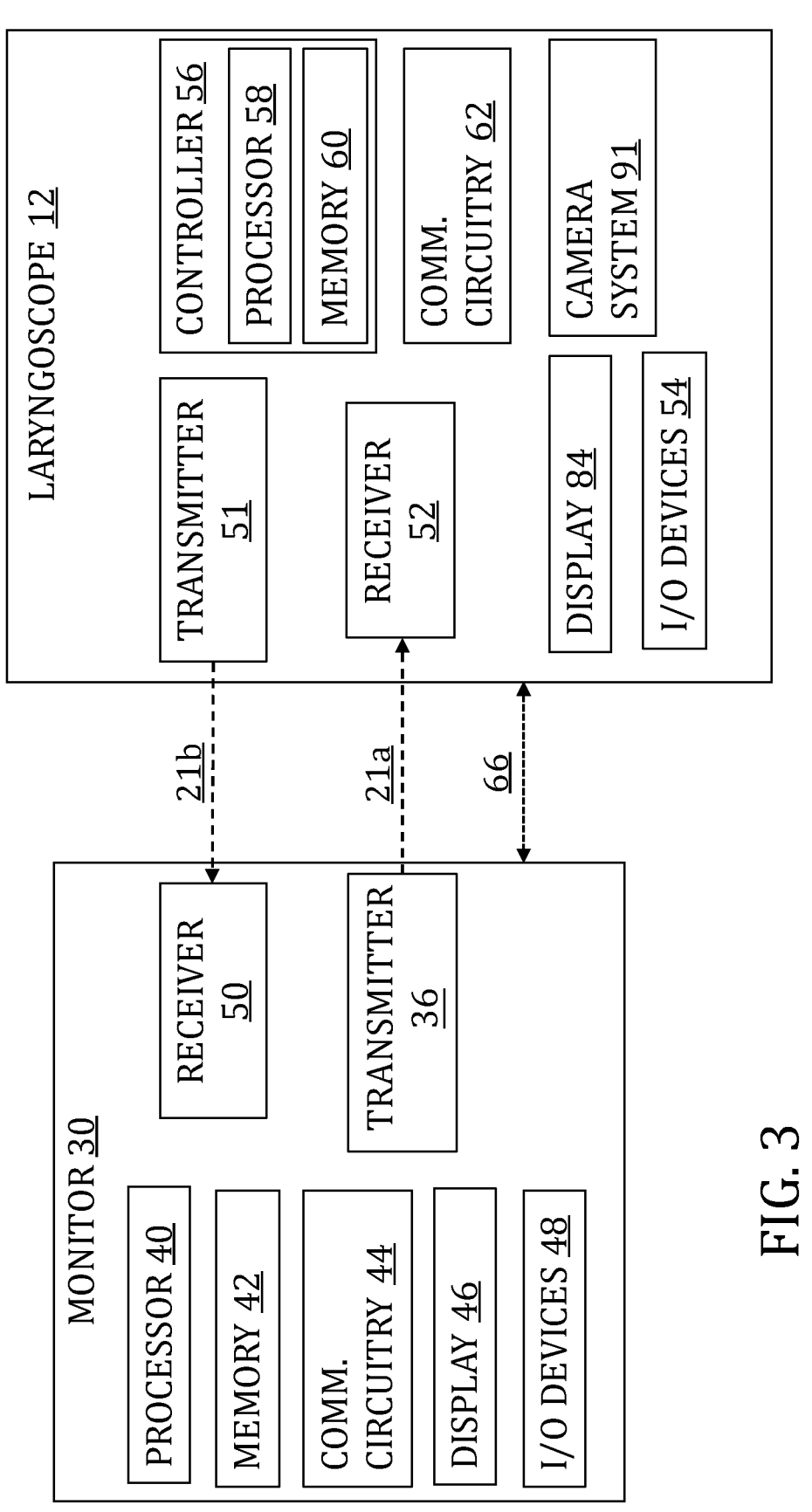
FIG. 3 depicts an example block diagram of the monitor and the laryngoscope.

FIG. 2 depicts an example video laryngoscope 12 in communication with an example monitor 30. FIG. 3 depicts an example block diagram of the monitor 30 and the laryngoscope 12. FIGS. 2-3 are discussed concurrently.

The monitor 30 and the video laryngoscope 12 may include various components that enable the medical device monitoring system 10 to carry out the techniques disclosed herein. For example, the monitor 30 may include an infrared transmitter 36, an infrared receiver 50, one or more processors 40, a hardware memory 42, a communication circuitry 44, a display 46, and input/output (I/O) devices 48. The monitor 30 may be powered by various power sources, such as a battery or input from an external power source.

The laryngoscope 12 may include an infrared receiver 52, an infrared transmitter 51, a camera system 91, I/O devices 54 (e.g., touch sensor), a controller 56 (e.g., electronic controller), one or more processors 58, a hardware memory 60, and/or communication circuitry 62. As should be understood, the monitor 30 and/or the laryngoscope 12 may include additional, or fewer, components as well.

The communication circuitry 44, 62 may include wireless transceivers that are configured to establish wireless communication with one another. By way of example, the communication circuitry 44, 62 may be configured to communicate using the IEEE 802.15.4 standard, and may communicate, for example, using ZigBee, WirelessHART, or MiWi protocols. Additionally or alternatively, the communication circuitry 44, 62 may be configured to communicate using the BLUETOOTH standard or one or more of the IEEE 802.11 standards. In some examples, the communication circuitry 44, 62 may be provided in an adapter (e.g., a dongle) that is configured to couple to the monitor 30 and/or laryngoscope 12 to facilitate wireless communication 66 between the monitor 30 and the laryngoscope 12.

In an example, the wireless video laryngoscope 12 pairs with other devices (such as the monitor 30, display 33, wireless hub 24, or other devices separate from the laryngoscope 12) through the transmission and receipt of infrared signals. Infrared remote control or communication uses optical signals transmitted from an infrared emitter and received by an infrared receiver in transmission range of the infrared emitter. The infrared signals may include identification information that identifies the emitting device, such as a media access control (MAC) address, an IP address, a unique device identifier, and the like. This unique identification information is then used to pair the emitting and receiving devices together for further wireless communication. Once paired the devices utilize other wireless transceivers (not infrared) to send and receive information wirelessly, such as to stream video data from a wireless video laryngoscope to an external display screen.

More specifically, the laryngoscope 12 may pair and communicate medical device data (e.g., acquired by camera system 91) when the laryngoscope 12 receives a resolvable infrared signal 21. In the illustrated example in FIG. 3, the monitor 30 transmits an infrared signal 21*a* that may include identification information that is unique the monitor 30. When the infrared signal 21*a* is resolvable, the laryngoscope 12 pairs with the monitor 30 that transmitted the infrared signal 21*a.*

The monitor 30 includes an infrared transmitter 36 that generally allows the monitor 30 to pair with the laryngoscope 12. More specifically, the transmitter 36 may emit, send, or transmit infrared signals that are received by an infrared receiver 52 of the laryngoscope 12 within a suitable range of the monitor 30. In an example, the infrared signals may be in a range of 700 nm to 1 mm. In one example, the infrared signal is a near infrared signal in a range of 750 nm-1400 nm. While, in some examples of the disclosure, the transmitter 36 is discussed as sending infrared signals, it should be noted that the transmitter 36 may be capable of emitting other types of electromagnetic signals within other bands of the electromagnetic spectrum. Further, while certain examples show the transmitter 36 on the monitor 30 and the receiver on the laryngoscope 12, it should be understood that, additionally or alternatively, these positions may be exchanged. Additionally, the receiver may be a transceiver that both transmits and receives signals, and the emitter may also be a transceiver that both transmits and receives signals.

To facilitate pairing, the monitor 30 may transmit the infrared signal 21*a* including identification information or data about the monitor. For example, the processor of the monitor 30 may output a control signal that causes the transmitter 36 of the monitor 30 to output the infrared signal 21*a.* The laryngoscope 12 receives the signal 21*a* and the identification information and uses that information to pair with the monitor 30. Pairing refers to establishing a wireless communication (other than infrared communication), such as between the monitor 30 and the laryngoscope 12. For example, the laryngoscope 12 may receive a resolvable infrared signal from the monitor 30 that includes a unique MAC address associated with the monitor 30. As such, the laryngoscope 12 may identify the monitor 30 on a network communicating with the laryngoscope and the monitor 30. Successful pairing may be indicated by establishing communication via wireless or Bluetooth circuitry and associated handshakes of the monitor 30 and the laryngoscope 12. The laryngoscope 12 may use the unique identification information provided by the monitor 30 to send the appro priate code, key, and/or device identifier to establish the communication with the monitor 30. Once the devices are paired, the monitor 30 receives medical device data from the laryngoscope 12. Additional details regarding pairing of the video laryngoscope 12 and the monitor 30, external display 33, and/or the wireless hub 24 are discussed in International Application No. PCT/CN2020/112053, titled System and Method for Pairing Medical Devices, filed on Aug. 28, 2020, which is incorporated herein by reference in its entirety.

In some examples, the video laryngoscope 12 may also or alternatively include an infrared transmitter 51 that transmits an infrared signal 21b to the receiver 50 of the monitor 30. In such examples, the video laryngoscope 12 may transmit identifying information to the monitor 30 that completes the pairing process. In some examples, the infrared receivers 50, 52 and the infrared transmitters 36, 51 may be used to exchange identification, authentication, and/or other pairing data between the monitor 30 and the video laryngoscope 12 via infrared signals 21a, 21b. Such an exchange of data may further reduce user interactions with the monitor 30 and/or the video laryngoscope 12 to complete the pairing process.

In one example, the monitor 30 may deactivate the transmitter 36 of the monitor in response to pairing with the medical device. For example, the monitor 30 may output a control signal that causes the transmitter 36 to halt transmission. In this manner, the monitor 30 pairs to a single laryngoscope 12. The laryngoscope 12 may pair to only a single monitor 30 by automatically deactivating the receiver 52 upon successful pairing. In another example, the laryngoscope 12 may be configured to pair to any available monitor 30 or multiple monitors or external devices, and the receiver 52 is active during the powered-on state of the laryngoscope 12 or until actively turned off by user input.

In some examples, the monitor 30 and the laryngoscope 12 may include electrical circuitry configured to process signals, such as signals generated by the camera system 91, and/or control signals provided via inputs, such as the inputs 48 of the monitor 30, or the inputs 54 on the laryngoscope 12, for example. In the illustrated example, the processors 40, 58 may be used to execute software. For example, the processor 58 of the laryngoscope 12 may be configured to receive signals from the camera system 91 and execute software to generate an image and/or to carry out any of a variety of processes in accordance with the present disclosure (e.g., display the image, store the image, transfer the image, or the like). Moreover, the processors 40, 58 may include multiple microprocessors, one or more "general-purpose" microprocessors, one or more special-purpose microprocessors, and/or one or more application specific integrated circuits (ASICS), or some combination thereof. For example, the processors 40, 58 may include one or more reduced instruction set (RISC) processors. It should be appreciated that the various processing steps may be carried out by either processor 40, 58 or may be distributed between the processors 40, 58 in any suitable manner.

The hardware memory 42, 60 may include a volatile memory, such as random access memory (RAM), and/or a nonvolatile memory, such as read-only memory (ROM). It should be appreciated that the hardware memory 42, 60 may include flash memory, a hard drive, or any other suitable optical, magnetic, or solid-state storage medium, other hardware memory, or a combination thereof. The memory 42, 60 may store a variety of information and may be used for various purposes. For example, the memory 42, 60 may store processor-executable instructions (e.g., firmware or software) for the processors 40, 58 to execute, such as instructions for generating and reading the infrared signals

21. As discussed herein, the transmitter 36 may transmit identification information associated with the monitor 30, such as a MAC address, an IP address, a passkey, and the like. The processor 40 may retrieve the identification information from the memory and/or storage 42 and cause the transmitter 36 to emit an infrared signal 21 that includes the identification information. The processors 40, 58 may also be used to validate the pairing between the video laryngoscope 12 and the monitor 30 (and/or other external devices).

The video laryngoscope 12 includes a display portion 82 having a display screen 84 that is configured to display images or other data, and body portion 88 with a handle portion or handle 86 that is configured to be gripped by the medical professional during the laryngoscopy procedure, and an elongate portion or arm 90 that supports the camera assembly or system 91 that is configured to obtain images (e.g., still images and/or moving images, such as videos). In use, the arm 90 may include or support a removable laryngoscope blade 92 that is detachable from the handle 86. The camera assembly 91 may include a camera stick that resides within the blade 92 when the blade is attached to the handle 86. The display screen 84 may be pivotably coupled or attached to the handle 86 such that a user may pivot the display screen 84 relative to the handle 86. In some examples, the display portion 82 and the body portion 88 may not be distinct portions, such that the display screen 84 is integrated into the body portion 88.

The video laryngoscope 12 may also include a power button 94 that enables a medical professional to power the laryngoscope 12 off and on. In one example, the power button 94 may directly control operation of the receiver 52 and/or transmitter 51, such that the receiver 52 and/or transmitter 51 activates upon powering on of the video laryngoscope 12. In the illustrated example, the video laryngoscope 12 includes an input button, such as a touch or proximity sensor 96 (e.g., capacitive sensor, proximity sensor, or the like) that is configured to detect an object (e.g., a finger or stylus). The touch sensor 96 may enable the medical professional operating the video laryngoscope 12 to efficiently provide inputs or commands, such as inputs that cause the camera (e.g., medical sensor) to obtain or store an image on a memory of the laryngoscope and to validate pairing with the monitor 30.

The video laryngoscope 12 may be configured to communicate with the monitor 30 and/or other remote devices or systems via any of a variety of techniques. For example, as discussed above with respect to FIG. 3, the video laryngoscope 12 and the monitor 30 may include the communication circuitry 62 and 44, respectively, which may be wireless transceivers that are configured to establish wireless communication with one another using any suitable protocol. In some examples, in response to detection of a resolvable infrared signal 21 by the receiver 52, the video laryngoscope 12 automatically transmits data from the storage device of the video laryngoscope 12 to the monitor 30 and/or transmits data to one or more other remote devices or systems at certain times. In the example depicted in FIG. 2, the receiver 52 and transmitter 51 are disposed within a housing of the of the display portion 82 and the infrared signals 21a, 21b are passed through an infrared window of the housing, as discussed further below. However, in other examples, the receiver 52 and/or transmitter 51 may be disposed on or in the handle 86 or body portion 88.

In the illustrated example, an adapter 98 (e.g., wireless adapter, dongle, or bridge device) is provided to facilitate wireless communication between the video laryngoscope 12 and the monitor 30 and/or other remote devices and systems.

That is, the adapter 98 may include the communication circuitry 44 and/or the transmitter 36. In some examples, the adapter 98 may be the wireless hub 24 discussed above in FIG. 1.

The monitor 30 may also display screen 100 (e.g., touchscreen display) that is configured to provide information to the medical professional and/or that is configured to receive inputs. For example, the monitor 30 may provide a still or moving image 102 obtained by the camera assembly 91 of the video laryngoscope 12, and in some cases, may also provide information obtained via various physiological sensors (e.g., heart rate, oxygen saturation, or the like). In some examples, the image 102 may be a video that is streamed wirelessly in substantially real-time from the video laryngoscope 12 to the monitor 30. The video laryngoscope 12 and the monitor 30 may interact to carry out various other advanced monitoring functions, such as transfer of data (e.g., images, time data, or the like) from the video laryngoscope 12 to the monitor 30 in response to an input received (e.g., a touch input from the user at the video laryngoscope 12 and/or at the monitor 30) and/or automatic transfer of data from the video laryngoscope 12 to the monitor 30 at certain times (e.g., upon powering the video laryngoscope 12 and/or the monitor off or on, periodically during the laryngoscopy procedure, upon receipt of a user input, upon receipt of an input indicating that the laryngoscopy procedure is complete and/or that certain steps of the laryngoscopy procedure are complete). The monitor 30 may include various other features, such as a power button 108 that enables a user to power the monitor 30 off and on. It should be appreciated that the video laryngoscope 12 and the monitor 30 may also include ports (e.g., USB ports, Ethernet ports, high-definition multimedia interface (HDMI) ports, optical ports, infrared ports, near field ports, or the like) that enable the components to be coupled to one another and/or to other components (e.g., computing systems or storage systems) via a wired connection.

In some examples, the display screen 100 of the monitor 30 and/or the display screen 84 of the video laryngoscope 12 may be configured to provide an indication that the monitor 30 and the video laryngoscope 12 are communicatively coupled or paired to one another. In some examples, the video laryngoscope 12 may be configured to provide a laryngoscope ID (e.g., numerical or descriptive identifier) to the monitor 30, and the monitor 30 is configured to display the laryngoscope ID on the display screen 100 to enable the medical professional to confirm that the monitor 30 is receiving data from the appropriate video laryngoscope 12. The monitor 30 may be configured to connect to one or more video laryngoscopes 12 at a time.

Additionally or alternatively, in some examples, the monitor 30 may be configured to provide a monitor ID (e.g., the identification information) to the video laryngoscope 12, and the video laryngoscope 12 is configured to display the monitor ID on the display screen to enable the medical professional to confirm that the laryngoscope 12 is transferring data to the appropriate monitor 30. In some examples, the monitor 30 and/or the video laryngoscope 12 may enable the medical professional to provide inputs (e.g., via one or more touchscreen display screens 84, 100) to adjust or to select the appropriate device(s) (e.g., the monitor 30 and the video laryngoscope 12) that should communicate with one another during the laryngoscopy procedure.

While the systems disclosed herein describe a video laryngoscope 12, other medical devices with the infrared technology described herein may also be used. For example, medical devices such as an endoscope, a handle or controller for an imaging tool, a medical sensor, and/or another wireless medical tool may be utilized.

Figure 5:
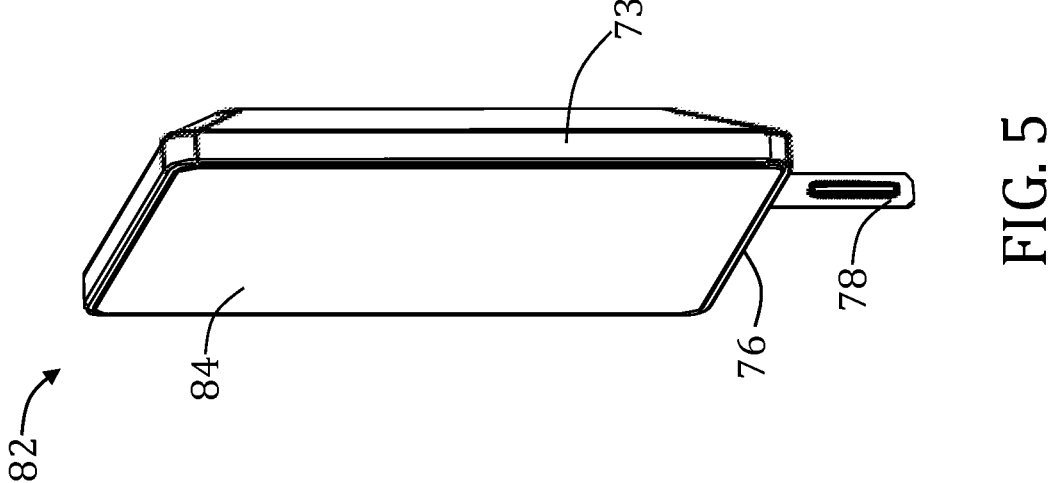
FIG. 5 is a perspective view of a front side of the housing of the example video laryngoscope depicted inf FIG. 4.
Figure 4:
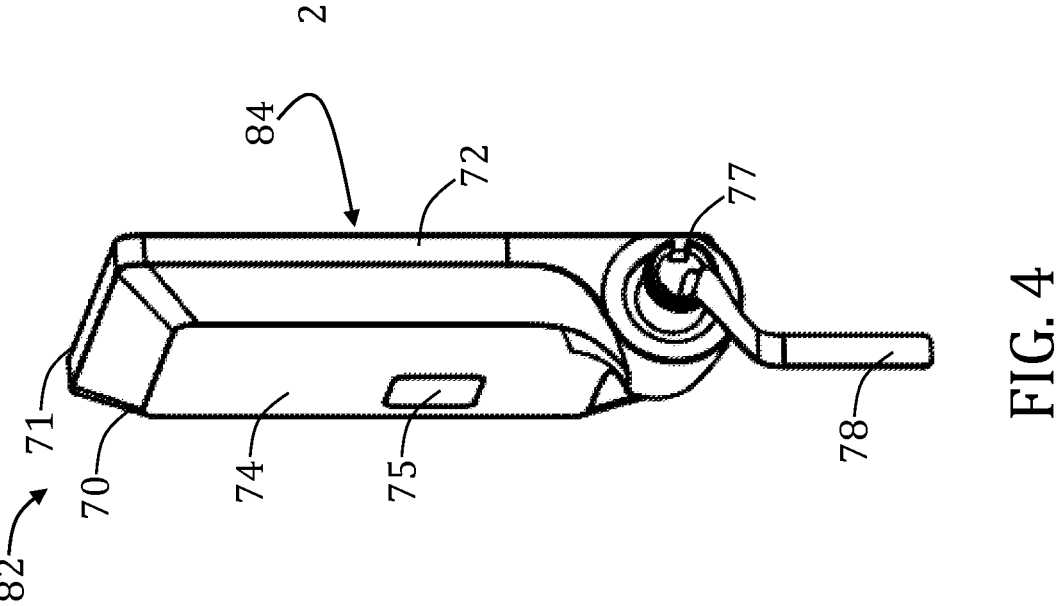
FIG. 4 is a perspective view of a rear side of a housing of an example video laryngoscope.

FIG. 4 is a perspective view of a rear side of a housing 70 of a video portion 82 of an example video laryngoscope 12. FIG. 5 is a perspective view of a front side of the housing 70 of the video portion 82 of the example video laryngoscope depicted in FIG. 4. FIGS. 4-5 are discussed concurrently.

The video portion 82 of the video laryngoscope 12 includes a cabinet or housing 70 that houses electronic components of the display portion 82, such as the memory, processor, video display components, communication circuity, and other computing components as discussed above. The housing 70 also houses the infrared transmitter and/or infrared receiver of the video laryngoscope 12. The housing 70 includes a top side 71, a left side 72, a right side 73, a back side 74, and a bottom side 76. The front side of the housing 70 includes the display screen 84 which may substantially fill the entirety of the front side of the housing 70. The terms "left," "right," "top," and "bottom" are from the perspective of a clinician viewing the display screen 84 during use of the video laryngoscope 12. During use, the back side 74 faces away from the clinician and towards the patient. Accordingly, the back side 74 may be referred to as the patient-facing side and the front side may be referred to as the user-facing or clinician-facing side.

To allow for infrared signals (e.g., infrared light or electromagnetic radiation) to be transmitted from and/or received by the components within the housing 70, the housing 70 includes an infrared window 75. The infrared window 75 is made from a different material than other portions of the housing 70. For instance, the infrared window 75 is made from a material that is translucent to the infrared spectrum encompassing the infrared range of the infrared signals used by the video laryngoscope 12. As an example, the infrared window 75 may be made from a polycarbonate material that is translucent in the infrared spectrum but opaque to the visible spectrum (specifically a human-visible spectrum). Accordingly, the human eye cannot see through the infrared window 75, and the infrared window 75 may appear black to the human eye.

By placing the infrared window 75 on the back side 74 of the housing 70, the infrared signals may be more easily received from, or transmitted to, a monitor or other device within the same room. For instance, the line of sight between the infrared window 75 and an infrared receiver is more likely to be established between the back side 74 and the monitor, as compared to having the infrared window 75 on the front side of the housing 70. For example, with the infrared window 75 on the front side of the housing 70, the clinician may occlude a line of sight between the infrared window 75 and the other monitors or devices in the room. However, in some examples, a clinician may wear a wireless hub around his or her neck (as shown in FIG. 1). In such systems, the infrared window 75 may be included on the front side and/or top side 71 of the housing 70 instead of, or in addition to, the infrared window 75 on the back side 74 of the housing 70.

In the example depicted, the back side 74 is a substantially planar surface. However, in other examples, the back side 74 may be a curved or contoured surface. For instance, in other examples the housing 70 may have a partial spherical shape, a dome shape, and/or an ovoid shape, among other types of shapes. In such examples, the infrared window 75 may be contoured to match the shape of the surrounding surface of the back side 74.

In other examples, the infrared window 75 and the infrared transmitter and/or receiver may be positioned in other portions of the video laryngoscope 12. For instance, the infrared window 75 may be placed in the handle of the video laryngoscope 12. Depending on the configuration of the handle, however, placing the infrared window 75 on the handle may be disadvantageous because the clinician's hand may occlude the infrared window 75 when the video laryngoscope 12 is in use. Similarly, including the infrared window 75 on the laryngoscope blade would likely result in the same occlusion issues because, during use, the blade is located within the patient.

With the infrared window 75 being located on the back side 74, a direct line of sight between the infrared window 75 and the monitor or other device still may not need to be established. Because many objects within a hospital environment or operating room are reflective of infrared light, the infrared signals that are emitted may reflect off various surfaces and then be received or detected by the respective infrared receivers. As such, the infrared window 75 may not need to be directly aligned with the monitor.

The bottom side 76 of the housing 70 also includes a pivot component 77, which may a portion of a cylinder. The pivot component 77 connects to the handle of the video laryngoscope 12 to allow for the video laryngoscope 12 to rotate or pivot relative to the handle.

A video connector 78 may also protrude through the pivot component 77 such that the video connector 78 may extend into the handle when the display portion 82 is attached or coupled to the handle. The video connector 78 connects with elements of the camera system to allow for video data captured by the camera system to be transferred to the display screen 84 via the video connector 78.

Figure 6:
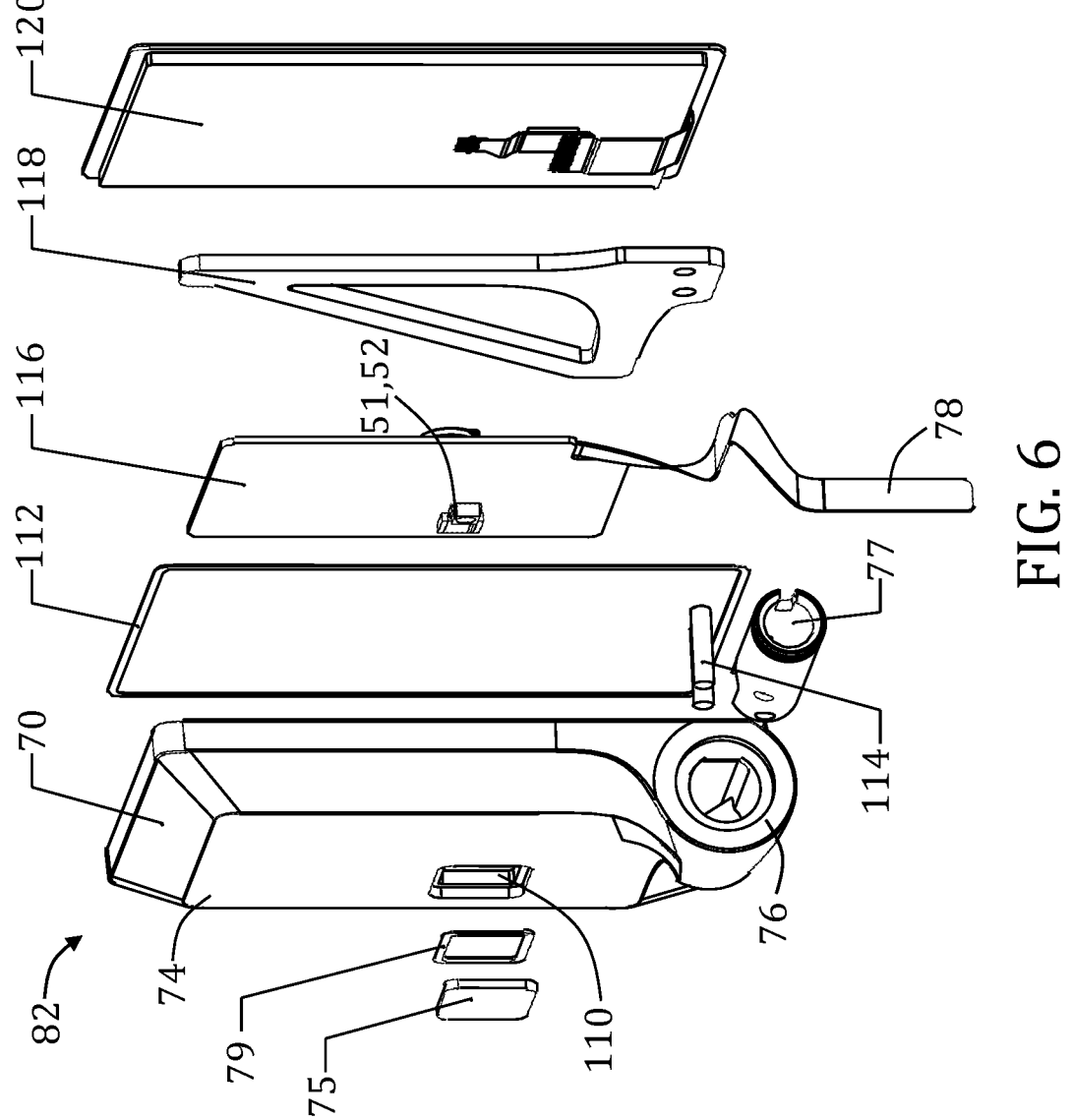
FIG. 6 depicts an exploded view of a display portion of the video laryngoscope.

FIG. 6 depicts an exploded view of the display portion 82 of the video laryngoscope 12. The construction and assembly of the infrared window 75 can be more clearly seen from the exploded view in FIG. 6. During assembly, the infrared window 75 is inserted into a recess of the back side 74 of the housing 70. The infrared window 75 may be sized based on the size of the recess such that the perimeter of the infrared window 75 substantially matches the interior surface of the recess. The recess includes a ledge and an opening or through hole 110 through which the infrared signals pass. The ledge may extend around the perimeter of the hole 110. When the infrared window 75 is inserted into the recess, the infrared window 75 rests on, or is supported by, the ledge of the recess.

A window sealant 79 may be positioned between the infrared window 75 and ledge. The window sealant 79 may be an adhesive tape or sealant that bonds the infrared window 75 to the ledge. The window sealant 79 extends around an outer edge of the infrared window 75 but does not occlude a central region of the infrared window 75 so as not to occlude the infrared signals passing through the infrared window 75. The adhesive properties of the window sealant 79 may be pressure activated such that pressure applied when inserting the infrared window 75 into the recess causes the adhesive to activate and bond the infrared window 75 to the ledge of the recess of the back side 74. By sealing the infrared window 75 with the window sealant 79, the video laryngoscope 12 may remain substantially waterproof or water resistant, which allows for the video laryngoscope 12 to be cleaned and disinfected for reuse with different patients.

The bottom side 76 of the housing 70 may include a bore for receiving the pivot component 77. For instance, as discussed above, the pivot component 77 may be a cylindrical component. That cylindrical component is received in the bore of the bottom side 76. The cylindrical component may similarly be received or coupled to a portion of the handle.

The display portion 82 may also include a video panel sealant 112, one or more standoff pins 114, a support structure 118 (e.g., a roll cage), and a video panel 120. The video panel 120 may be joined together with the remainder of the housing 70 via the video panel sealant 112. The video panel sealant 112 may have substantially the same properties as the window sealant 79. For instance, the video panel sealant 112 may be an adhesive tape. Thus, when the housing 70 is pressed together with the video panel 120 with the video panel sealant 112 located in between, the housing 70 is bonded to the video panel 120. Such a bonding with the video panel sealant 112 also provides water resistance to allow for cleaning and disinfection of the video laryngoscope 12.

The pins 114 and the support structure 118 provide additional structural support for the display portion 82. For instance, the pins 114 may extend from an interior surface of the back side 74 to an interior side of the video panel 120. Thus, the pins 114 help prevent the back side 74 and/or the video panel 120 from bending or moving inward towards the cavity defined by the housing 70 and the video panel 120 when assembled.

The support structure 118 provides support around the interior perimeter of the housing 70. The support structure 118 also provides a diagonal cross beam for structural rigidity. The diagonal cross beam extends from a top corner of the housing 70 to a bottom corner of the housing 70. The support structure 118 may also include through holes for receiving the pins 114.

The auxiliary board 116 may be a printed circuit board (PCB) or other type of circuit board on which the computing and other electrical components of the display portion 82 may be attached. For instance, as shown in FIG. 6, the infrared transmitter 51 (e.g., light-emitting diode (LED) and the infrared receiver 52 (e.g., diode) are attached to the auxiliary board 116. More specifically, the transmitter 51 and the receiver 52 are attached to a back surface of the auxiliary board 116 that faces the back side 74 of the housing 70. The transmitter 51 and the receiver 52 are positioned on the auxiliary board 116 at a location that is optically aligned with the infrared window 75. Accordingly, infrared light emitted from the transmitter 51 can propagate through the infrared window 75, and infrared light emitted from other sources that propagates through the infrared window 75 can be detected by the infrared window 75. Additional computing components and/or video processing components may be attached to the front side of the auxiliary board 116 facing the display screen 84.

When the display portion 82 is assembled, the emitting surface of the transmitter 51 and the receiving surface of the receiver 52 are optically aligned with the infrared window 75 and may be substantially near (e.g., less than 1 or 2 mm) the interior surface of the infrared window 75. Accordingly, the field of view of the transmitter 51 and the receiver 52 is near 180 degrees. However, due to the thickness of the infrared window 75, which may be about 2 mm or less, and the recessed position of the transmitter 51 and the receiver 52, the field of view may be less than a full 180 degrees. For example, the field of view may be greater than 150 degrees but less than or equal to 180 degrees. In general, the field of view may be considered hemispherical.

The video connector 78 may also extend from the auxiliary board 116. Accordingly, data can be exchanged between the electronic components attached to the auxiliary board 116 and the camera assembly to which the video connector 78 is coupled when the video laryngoscope 12 is fully assembled.

Figure 7:
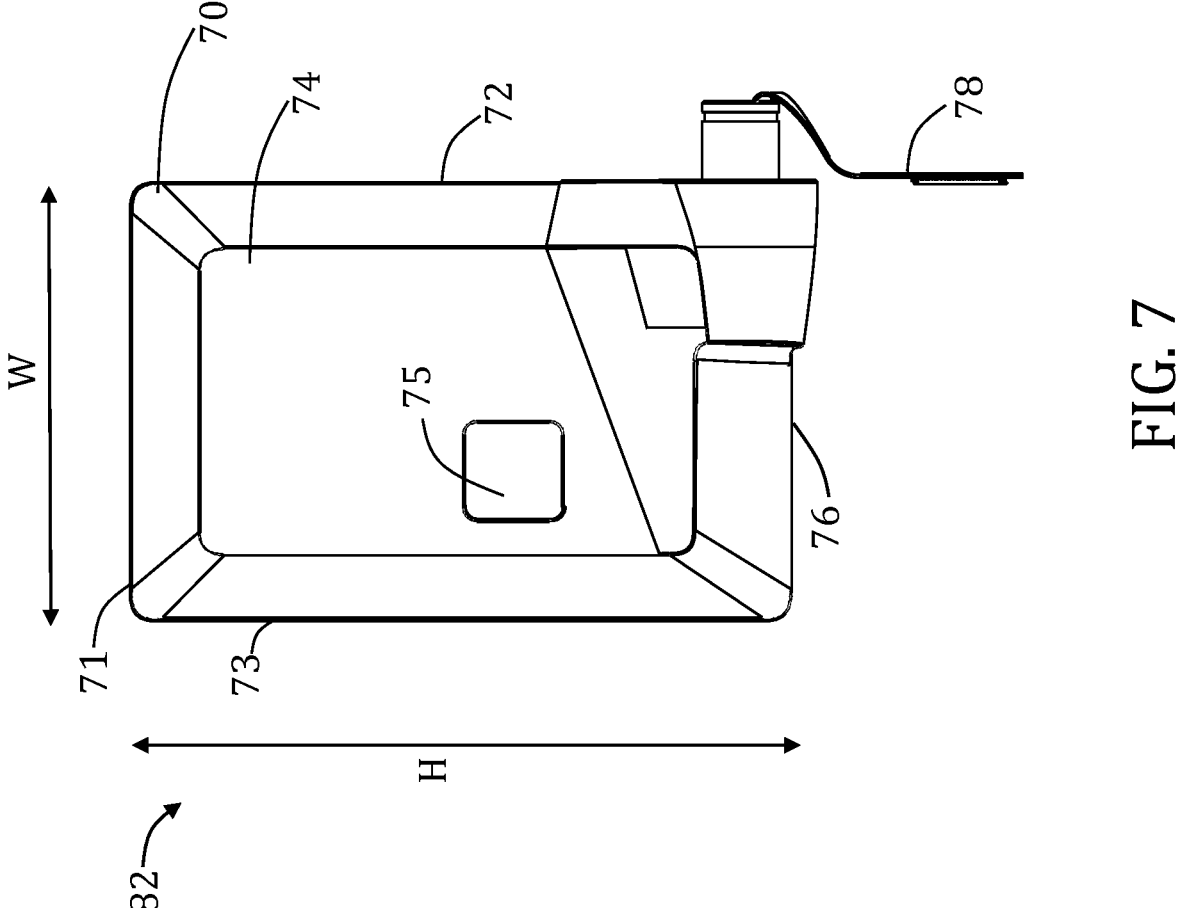
FIG. 7 depicts a rear view of the display portion of the video laryngoscope.

FIG. 7 depicts a rear view of the display portion 82 of the video laryngoscope 12. The housing 70 of the display portion 82 may be described as having a height (H) and a width (W). The height may be defined as the maximum distance from the top side 71 to the bottom side 76 measured in a top-to-bottom direction. The width may be defined as the maximum distance from the left side 72 to the right side 73 measured in a left-to-right direction.

The infrared window 75 may similarly have a height and a width. While, in the example depicted, the infrared window 75 has a square or rectangular shape, in other examples, the infrared window 75 may have a different shape, such as circle or oval shape. In such examples, the size of the infrared window 75 may be described by its diameter and/or the diameter of the major or minor axis.

The height of the infrared window 75 may be between about 5-10 mm and the width of the infrared window 75 may also be between about 5-10 mm. In some examples, the height of the housing 70 may be about 6-8 times greater than the height of the infrared window 75 or less than 7 times greater than the height of the infrared window 75. The width of the housing 70 may be about 4-6 times greater than the width of the width of the infrared window 75 or less than 6 times greater than the width of the infrared window 75. By sizing the infrared window 75 in such a manner, there is still substantial surface area on the back side 74 for the clinician to place his or her hand to manipulate the display portion 82 without occluding the infrared window 75.

The location of the infrared window 75 may be selected also to help prevent occlusion by the hand of clinician. For instance, the infrared window 75 may be positioned to provide a larger contiguous surface area on the back side 74 that does not encompass the infrared window 75. For instance, in the example depicted, the infrared window 75 is in the lower-right quadrant of the back side 74. Thus, the remainder of the quadrants are free from the infrared window 75 and available to be touched without occlusion from the hand of a clinician. In other examples, the infrared window 75 may be positioned such that the entirety of the infrared window 75 is within one quadrant of the back side 74, which may leave the remaining three quadrants available for physical touch without occluding the infrared window 75.

Figure 8:
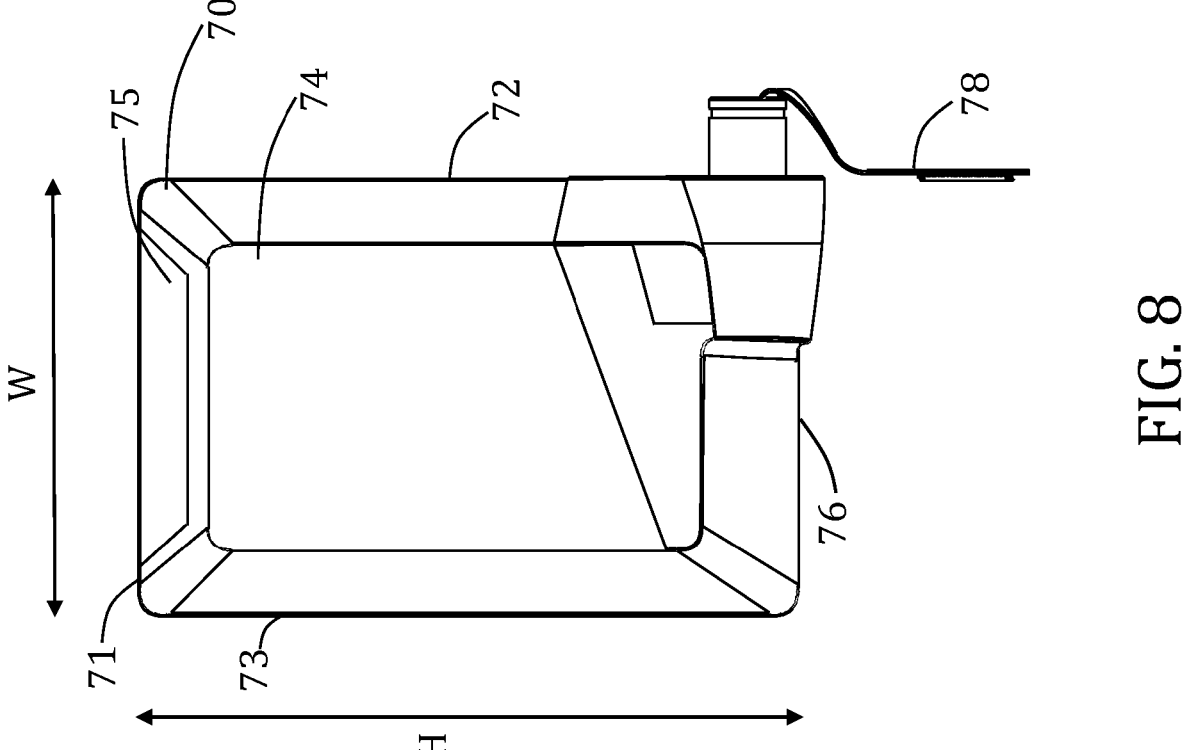
FIG. 8 depicts a rear view of the display portion of another example video laryngoscope.

FIG. 8 depicts a rear view of the display portion 82 of another example video laryngoscope 12. In the example video laryngoscope 12 of FIG. 8, the infrared window 75 is located in a different position from the examples described above in FIGS. 2-7. Instead of having the infrared window 75 entirely on the back side 74 of the housing 70, the infrared window 75 is positioned on the top side 71 of the housing 70. In the example depicted in FIG. 8, the infrared window 75 extends across a portion of the top side 71 and a portion of the back side 74. The infrared window 75 may still be one contiguous component, such as a single piece of polycarbonate, and the infrared window 75 may be attached to the housing 70 using similar techniques as discussed above (e.g., adhesive tape).

In examples where the infrared window 75 is located on the top side 71, the infrared window 75 may have a width that is at least 80% of the width of the housing 70. The height of the infrared window 75 may be less than about 20% or 10% of the height of the housing 70. Locating the infrared window 75 on the top side 71 and back side 74 of the housing increases the field of view of the transmitter and receiver behind the infrared window 75. However, locating the infrared window 75 in such a position presents additional manufacturing challenges in attaching the infrared window 75 to the housing 70 because the infrared window 75 tends to be angled or contoured.

While the above examples include an infrared window incorporated directly into the housing of the video portion of the laryngoscope, in other examples, the infrared receiver and/or transmitter may be mounted to the video laryngoscope, such as on the housing of the video portion of the video laryngoscope. For instance, the infrared receiver and/or transmitter may be mounted to the back side of the housing of the video portion. In such examples, the infrared receiver and/or transmitter may be incorporated into a secondary housing with an infrared window, and that secondary housing is attached or coupled to the primary housing of the video portion of the video laryngoscope.

While the disclosure may be susceptible to various modifications and alternative forms, specific examples have been shown by way of example in the drawings and have been described in detail herein. However, it should be understood that the examples provided herein are not intended to be limited to the particular forms disclosed. Rather, the various examples may cover all modifications, equivalents, and alternatives falling within the spirit and scope of the disclosure as defined by the following appended claims Those skilled in the art will recognize that the methods and systems of the present disclosure may be implemented in many manners and as such are not to be limited by the foregoing aspects and examples. In other words, functional elements being performed by a single or multiple components, in various combinations of hardware and software or firmware, and individual functions. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, a myriad of software/hardware/firmware combinations are possible in achieving the functions, features, interfaces and preferences described herein.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A video laryngoscope comprising:
a handle;
a housing, coupled to the handle, comprising a user-facing side, a patient-facing side, a top side, and a bottom side;
a display screen, coupled to the housing, and positioned in the user-facing side;
a camera coupled to the handle;
an infrared window positioned in at least one of the patient-facing side or the top side of the housing;
an infrared receiver, disposed in the video laryngoscope, that receives an infrared signal through the infrared window; and
a processor, disposed in the video laryngoscope, that validates a pairing between the video laryngoscope and an external device based on the infrared signal.

2. The video laryngoscope of claim 1, wherein the infrared window is positioned in the patient-facing side.

3. The video laryngoscope of claim 1, wherein the infrared window is positioned in the top side.

4. The video laryngoscope of claim 1, wherein the infrared window is entirely encompassed within a quadrant of the patient-facing side.

5. The video laryngoscope of claim 4, wherein the quadrant is a lower-right quadrant of the patient-facing side.

6. The video laryngoscope of claim 1, wherein the infrared window is provided in the handle.

7. The video laryngoscope of claim 1, wherein the display screen is configured to display images captured by the camera.

8. A video laryngoscope comprising:
a handle;
a camera coupled to the handle;
a display portion comprising a housing coupled to the handle, the housing having a user-facing side and a patient-facing side, and the housing comprising:
a display screen positioned on the user-facing side; and
an infrared window positioned on the patient-facing side;
at least one an infrared receiver or an infrared transmitter disposed within the housing and optically aligned with the infrared window; and
a processor, disposed within the video laryngoscope, that validates a pairing between the video laryngoscope and an external device based on an infrared signal.

9. The video laryngoscope of claim 8, wherein the patient-facing side is substantially planar.

10. The video laryngoscope of claim 8, wherein:
the housing has a height and a width;
the infrared window has a height and a width; and
the height of the housing is less than 7 times greater than the height of the infrared window.

11. The video laryngoscope of claim 10, wherein the width of the housing is less than 6 time greater than the width of the infrared window.

12. The video laryngoscope of claim 11, wherein the infrared window is entirely encompassed within a quadrant of the patient-facing side.

13. The video laryngoscope of claim 8, further comprising an adhesive tape, wherein:
the housing defines a recessed portion and a ledge; and
the adhesive tape is positioned between the infrared window and the ledge.

14. The video laryngoscope of claim 8, wherein the infrared window is translucent to an infrared spectrum and opaque to a human-visible spectrum.

15. A video laryngoscope system, comprising:
a video laryngoscope comprising:
a housing;
an infrared window in the housing; and
an infrared receiver, disposed within the housing, optically aligned with the infrared window;
an external display screen comprising an infrared emitter configured to be activated to emit an infrared signal comprising identification information of the external display screen; and
wherein the video laryngoscope is configured to receive the infrared signal through the infrared window provided in a housing of the video laryngoscope.

16. The system of claim 15, wherein the infrared window is disposed over an opening in the housing.

17. The system of claim 15, wherein the video laryngoscope further comprises a display screen coupled to the housing.

18. The system of claim 17, wherein the display screen is positioned on a front side of the housing and the infrared window is disposed on a back side of the housing.

19. The system of claim 15, wherein the video laryngoscope further comprises:
a handle pivotably coupled to the housing; and
a camera assembly coupled to the handle.

* * * * *